(12) United States Patent
Laramée et al.

(10) Patent No.: US 7,547,536 B1
(45) Date of Patent: Jun. 16, 2009

(54) METHOD FOR DETECTING BACTERIAL SPORES

(75) Inventors: James A. Laramée, Kansas City, MO (US); Robert B. Cody, Portsmouth, NH (US)

(73) Assignee: JEOL USA, Inc., Peabody, MA (US)

( * ) Notice: Subject to any disclaimer, the term of this patent is extended or adjusted under 35 U.S.C. 154(b) by 998 days.

(21) Appl. No.: 10/160,435

(22) Filed: May 31, 2002

(51) Int. Cl.
*C12Q 1/00* (2006.01)
*C12Q 1/24* (2006.01)
*C12N 3/00* (2006.01)
*C12N 1/00* (2006.01)
*C12N 1/38* (2006.01)

(52) U.S. Cl. .................. 435/242; 424/1.11; 424/1.17; 435/4; 435/7.2; 435/7.32; 435/30; 435/34; 435/243; 435/244; 435/252.1; 435/252.31; 436/161; 436/173; 436/174; 436/177

(58) Field of Classification Search .............. 435/1.3, 435/4, 5, 7.2, 7.32, 29, 30, 32, 34, 39, 40.15, 435/162, 173.7, 173.8, 173.9; 530/413, 415, 530/416, 417, 422; 96/101; 422/70, 73
See application file for complete search history.

(56) References Cited

U.S. PATENT DOCUMENTS

| | | | |
|---|---|---|---|
| 4,224,031 A * | 9/1980 | Mee et al. .................. 23/230 |
| 5,876,960 A | 3/1999 | Rosen .......................... 435/39 |
| 5,962,499 A * | 10/1999 | Meinke et al. .............. 514/410 |
| 6,103,906 A | 8/2000 | Roduit et al. ............... 546/327 |
| 6,228,654 B1 | 5/2001 | Chait et al. .................. 436/94 |

OTHER PUBLICATIONS

Beverly et al. 2000. Anal. Chem. vol. 72: 2428-2432.*
Beverly et al. 1996. Rapid Comm. in Mass Spectro. vol. 10:455-458.*
Synder et al. 1996. Field Anal. Chem. and Tech. vol. 1(1):49-58.*
Beverly et al., "Analysis of Dipicolonic acid in Bacterial Spores by Electron Monochromator-Mass Spectrometry," *47th ASMS Conference on Mass Spectrometry and Allied Topics*, Dallas, Texas, Jun. 1999.
Beverly et al., "Electron Monochromator Mass Spectrometry for the Analysis of Whole Bacteria and Bacterial Spores," *Analytical Chemistry*, vol. 72, No. 11, pp. 2428-2432, Jun. 2000.

* cited by examiner

*Primary Examiner*—Robert B Mondesi
*Assistant Examiner*—J. Hines
(74) *Attorney, Agent, or Firm*—The Webb Law Firm

(57) ABSTRACT

A method of detecting the presence and quantity of bacterial spores, which includes adding an electrophilic alcohol and an acid anhydride to a sample, admixing the sample with a solvent, and analyzing the sample. The sample may be analyzed by injecting the mixture into a gas chromatograph equipped with a mass spectra detector.

25 Claims, No Drawings

METHOD FOR DETECTING BACTERIAL SPORES

BACKGROUND OF THE INVENTION

1. Field of the Invention

This invention relates to a method for detecting bacterial spores using a combination of gas chromatography and mass spectrometry.

2. Description of Related Art

The detection of bacterial spores, or endospores, is useful for a wide variety of purposes. For example, potential biological agents used in warfare and by terrorists include spore-producing bacteria that cause diseases, such as anthrax, botulism, gas gangrene, and tetanus. The detection of spores of such bacteria can also be important in determining and implementing appropriate countermeasures against such agents. In agricultural technologies, spore-producing bacteria, such as *Bacillus thuringiensis*, are often used as insecticides. Spores in soil or plant samples can be monitored to ensure that the bacteria population is sufficiently high to be effective against insect pests. In the sanitation and hygiene fields, the detection of bacteria spores can be useful to monitor indoor environments, water quality, and food quality. In addition, the detection of nonviable bacterial spores can be useful to paleontologists.

Bacterial endospore concentrations are not easily determined with conventional techniques. Among the primary conventional techniques are microscopy and plate culture counting, both of which are extremely slow and tedious to perform.

U.S. Pat. No. 5,876,960 to Rosen discloses methods for detecting and quantifying bacterial spores in a sample. The method utilizes a lanthanide combined with a medium to be tested for endospore content. The lanthanide reacts with calcium dipicolinate, which is present in bacterial spores, to produce a lanthanide chelate, having distinctive absorbance and emission spectrums, which are detected using photoluminescence. This method is limited, however, as it is difficult to access dipicolinic acid because the endospore casing is difficult to penetrate.

Beverly et al., "Analysis of Dipicolinic acid in Bacterial Spores by Electron Monochromator-Mass Spectrometry," 47th *ASMS Conference on Mass Spectrometry and Allied Topics*, 1999 discloses a method of measuring dipicolinic acid in *Bacillus cereus* in which dried bacteria was directly introduced into a mass spectrometer and heated to 400° C. Bacteria spores typically contain from 7 to 14 percent by weight dipicolinic acid or salts thereof. Although the method was able to detect dipicolinic acid, the endospore casings were not reliably opened, making the results less than quantitative.

It would be desirable to develop a method for detecting bacterial spores that does not rely on time consuming and tedious microscopy and plate culture methods. Such a method should reliably and predictably open endospore casings so that the dipicolinic acid within can be accessed and measured as a surrogate for the quantity of bacterial spores present in a sample.

SUMMARY OF THE INVENTION

The present invention relates to a method of detecting the presence and quantity of bacterial spores. The method includes adding an electrophilic alcohol and an acid anhydride to a sample, admixing the sample with a gas chromatography solvent, and analyzing the sample. The sample may be analyzed using mass spectrometry, or other suitable methods of analysis.

DESCRIPTION OF THE PREFERRED EMBODIMENTS

Unless otherwise indicated, all numbers or expressions referring to quantities of ingredients, reaction conditions, etc. used herein are to be understood as modified in all instances by the term "about."

The present invention is directed to a method of detecting the presence and quantity of bacterial spores. The method includes adding an electrophilic alcohol and an acid anhydride to a sample, optionally drying the sample, admixing the sample with a gas chromatography solvent, and injecting the mixture. The analysis may be performed using mass spectrometry, gas chromatography coupled with mass spectrometry, or any other suitable method of analysis.

Any suitable electrophilic alcohol may be used in the present invention, so long as it is able to form a diester with dipicolinic acid. In an embodiment of the present invention, the electrophilic alcohol is present in an amount sufficient to convert greater than 75 percent by weight, typically, 90 percent by weight, in many cases, greater than 95 percent by weight, and in other cases, 100 percent by weight of the dipicolinic acid to a corresponding dipicolinic diester of the electrophilic alcohol.

Suitable electrophilic alcohols include any short chained aliphatic alcohol, typically, C1 to C8 aliphatic alcohols, containing an electron withdrawing group. Examples of suitable electron withdrawing groups include, but are not limited to, fluoro, chloro, bromo, iodo, nitro, cyano, and the like.

In an embodiment of the present invention, the electrophilic alcohol is pentafluoropropanol.

The derivatization of dipicolinic acid, i.e., the reaction of the electrophilic alcohol with dipicolinic acid to form the dipicolinic acid diester of the electrophilic alcohol, is shown in Scheme 1.

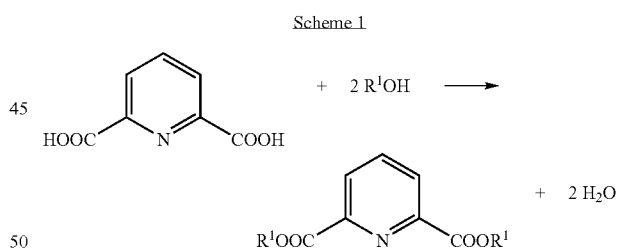

Scheme 1

In Scheme 1, $R^1OH$ represents an electrophilic alcohol. The formation of the dipicolinate diester generates water as a by-product. The derivatized dipicolinic acid is the species that may be detected when a sample is analyzed by an appropriate instrument.

In an embodiment of the present invention, in Scheme 1, R1 may be a group generally described by $CY_3CY_2(CH_2)_X$-, where X may range from 1-20, and each occurrence of Y is independently an electron withdrawing group as described above.

In a further embodiment of the present invention, a solvent used to dissolve the sample. The solvent may be, as a non-limiting example, a solvent suitable for use in gas chromatography. Any suitable gas chromatography solvent may be used in the present method as long as the derivitized dipicolinic acid is soluble therein. Suitable gas chromatography solvents include, but are not limited to, toluene, methylene chloride, xylene, hexafluorobenzene, hexane, acetone, ethyl acetate, benzene, and long chain aliphatic hydrocarbons, such as those greater then 3 carbon atoms in length.

As was mentioned above, bacterial spores typically have an endospore casing, which can prevent the dipicolinic acid contained within from being reliably accessed by known analytical methods. In the present invention, this limitation is overcome by selecting a suitable acid anhydride. A suitable acid anhydride is one that is able to reliably cause the endospore casing to open. The acid anhydride is present in an amount sufficient to cause the endospore casing to open.

In an embodiment of the present invention, the acid anhydride is an anhydride corresponding to a carboxylic acid with a pKa of less than 4, in many cases, less than 3, and typically, less than 2. The mixture in (a) may include the electrophilic alcohol and the acid anhydride in a volume ratio of 10:1, in some cases, 5:1, in other cases, 4:1, in some instances, 3:1, and in other instances, 2:1. The volume ratio of the electrophilic alcohol to the acid anhydride may be 1:1. Alternatively, the volume ratio of the electrophilic alcohol to the acid anhydride may be 1:10, in some cases, 1:5, in other cases, 1:4, in some instances, 1:3, and in other instances, 1:2. The volume ratio of the electrophilic alcohol to the acid anhydride may range between any values recited above.

The mixture in (a) is applied to a sample in an amount sufficient to open the endospore casing and derivitize the dipicolinic acid therein. The mixture in (a) may be applied to a sample in a weight ratio of mixture to sample of 10:1, in some cases, 5:1, in other cases, 4:1, in some instances, 3:1, and in other instances, 2:1. The weight ratio of the mixture in (a) to the sample may be 1:1. Alternatively, the weight ratio of the mixture in (a) to the sample may be 1:10, in some cases, 1:5, in other cases, 1:4, in some instances, 1:3, and in other instances, 1:2. The weight ratio of the mixture in (a) to the sample may range between any values recited above.

The opening of the endospore casing allows access to the dipicolinic acid, or its corresponding salts, within. This "opening" allows the electrophilic alcohol to react with, or derivatize, the dipicolinic acid to the corresponding dipicolinic diester. The derivatized dipicolinic acid may be subsequently detected by an appropriate instrument or analysis method.

The acid anhydride used in the present invention additionally functions to remove water from the sample, especially water produced as a by-product during the formation of the dipicolinic diester. In the present invention, the acid anhydride is present in an amount sufficient to react with all of such water produced product during the formation of the dipicolinic diester.

In a further embodiment of the present invention, the acid anhydride may be pentafluoropropionic acid anhydride or heptafluorobutyric acid.

Any suitable method may be used to dry the derivatized sample. As a non-limiting example, the derivatized dipicolinic acid may be dissolved in a low volatility solvent, such as, for example, toluene. The solution may then be passed through a thin bed of a suitable drying agent that will not react with the derivative, such as, for example, sodium sulfate. The bed may also contain a layer of an acid absorbing compound such as, for example, sodium carbonate or potassium carbonate. In an embodiment of the present invention, the two beds are held within a Pasteur pipet, and the derivatized dipicolinic acid is placed on top of the bed, and then the bed is washed with additional toluene and the eluent collected.

In the present invention, the sample is mixed with a suitable solvent, and the mixture is then analyzed. In an embodiment of the present invention, the mixture is injected into a gas chromatograph equipped with a mass spectra detector. Any suitable gas chromatograph may be used in the present invention. Suitable gas chromatographs will be able to volatilize the derivatized dipicolinic acid so that it may be detected. Suitable gas chromatographs that may be used in the present invention include, but are not limited to, Model 5890, available from Hewlett Packard, Palo Alto, Calif. and Model 3400, available from the Varian Instrument Company, Lexington, Mass.

Any suitable mass spectrometer may be used in the present invention. Suitable mass spectrometers will be able to identify and quantify the derivatized dipicolinic acid. Examples of suitable mass spectrometers include, but are not limited to, AccuTOF™ Time-of-Flight Mass Spectrometer, JMS-RSVP forward-geometry mass spectrometer, and GC Mate, SX102 and MStation reverse-geometry mass spectrometers all available from JEOL USA, Inc., Peabody, Mass.

In an embodiment of the present invention, the mass spectra detector is set to detect the radical anion of the dipicolinic diester of the electrophilic alcohol.

The mass spectra detector may use any suitable monitoring mode. Suitable monitoring modes are those that will enable detection and quantification of the derivatized dipicolinic acid. Suitable monitoring modes include, but are not limited to, low-resolution selected ion monitoring, high-resolution selected ion monitoring, and selected reaction monitoring.

In the present method, once the spores have been opened and the dipicolinic acid therein is derivatized, any suitable method of analyzing the sample for derivatized dipicolinic acid may be used. As a non-limiting example, a number of mass spectrometry methods may be used. For example, the sample may be introduced by a heated direct insertion probe and MS/MS methods and/or high-resolution mass spectrometry methods may be used to identify the derivative in the presence of interferences. Alternatively, a liquid chromatography/mass spectrometry method may be used, a nonlimiting example such being negative-ion atmospheric pressure chemical ionization, that can ionize electrophoric compounds by electron capture. Alternatively, "two-dimensional" gas chromatography, or GC/GC/MS, may be used. The GC/GC/MS method uses two gas chromatography columns. As a time-selected range of components elutes from the first column, they are introduced into a second GC column for further separation. The effluent from the second GC column is analyzed by mass spectrometry.

In a further embodiment of the present invention, ion mobility spectrometry may be used to analyze the derivatized sample. In ion mobility spectrometry, air is ionized by a weak radioactive source and the molecules of certain types of agent vapors are characterized by their ability to form low-mobility ionic clusters. These ionic clusters are then further classified according to their mobility relative to a known vapor source. Ion mobility spectrometry can be used in conjunction with other methods, such as mass spectrometry.

Example 1

Samples containing toluene, a mixture of 1 mg crushed rice in toluene and a sample containing a 1 mg portion of crushed rice from a sample containing 200 mg of rice contaminated with $10^8$ *Bacillus Subtillis* spores were prepared for injection. The plain rice and contaminated rice had been mixed with a derivatizing material, pentafluoropropanol and pentafluoropropionic anhydride, and dried prior to mixing with toluene.

The samples, along with the blank toluene sample, were injected into a gas chromatograph equipped with a mass spectrometer as a detector. The mass spectra detector included an electron capture ion source (Electron Monochromator, available from JEOL USA, Inc., Peabody, Mass.) and was set for negative-ion detection. The mass spectrometer was set to monitor at a mass-to-charge setting, m/z 431, which corresponds to the derivitized dipicolinic acid in the spores, in selected-ion monitoring mode. The spectra obtained for the toluene blank and the uncontaminated rice did not exhibit any discernable peaks. The spectra acquired from the contaminated rice sample had a peak indicating the presence of dipicolinic acid.

The invention has been described with reference to the preferred embodiments. Obvious modifications and alterations will occur to others upon reading and understanding the detailed description. It is intended that the invention be construed as including all such modifications and alterations insofar as they come with the scope of the appended claims or the equivalents thereof.

We claim:

1. A method for detecting the presence of bacterial spores in a sample comprising:

(a) adding to the sample an electrophilic alcohol and an acid anhydride of a carboxylic acid having a pKa of less than 4;

(b) admixing the sample with a solvent resulting in the opening of endospore casings of any bacterial spores in the sample and the formation of an ester between the electrophilic alcohol and dipicolinic acid contained within the bacterial spores; and (c) analyzing the sample using one or more analysis methods selected from the group consisting of gas chromatography (GC)/mass spectrometry (MS), GC/GC/MS, liquid chromatography/MS, ion mobility spectrometry and ion mobility spectrometry/MS;

wherein the analysis methods are capable of detecting a dipicolinic diester of dipicolinic acid and the electrophilic alcohol when bacterial spores are present in the sample.

2. The method of claim 1, wherein the electrophilic alcohol is a short chain alcohol that comprises at least one electron withdrawing group.

3. The method of claim 2, wherein the electron withdrawing group is one or more selected from the group consisting of fluoro, chloro, bromo, iodo, nitro, and cyano.

4. The method of claim 1, wherein the electrophilic alcohol is pentafluoropropanol.

5. The method of claim 1, wherein the solvent is a gas chromatography solvent.

6. The method of claim 5, wherein the gas chromatography solvent is one or more selected from the group consisting of toluene, methylene chloride, xylene, hexane, acetone, ethyl acetate, benzene, and long chain aliphatic hydrocarbons.

7. The method of claim 1, wherein the bacterial spores contain dipicolinic acid and the electrophilic alcohol is present in an amount such that the alcohol to anhydride volume ratio is from 10:1 to 1:10 to convert greater than 75 percent by weight of the dipicolinic acid to a corresponding dipicolinic diester of the electrophilic alcohol.

8. The method of claim 1, wherein the bacterial spores have an endospore casing, and the acid anhydride is present in an amount such that the volume ratio of the mixture in (a) to the sample is from 10:1 to 1:10 to cause the endospore casing to open.

9. The method of claim 7, wherein conversion of dipicolinic acid to dipicolinic diester produces water as a by-product, and the acid anhydride is present in an amount sufficient to react with all of such water produced to form the carboxylic acid corresponding to the acid anhydride.

10. The method of claim 1, wherein the acid anhydride is one or both of pentafluoropropionic acid anhydride and heptafluorobutyric acid.

11. The method of claim 1, wherein after (a), the sample is dried.

12. The method of claim 11, wherein the sample is dried by passing the solution from (a) through a bed of a drying agent and a layer of an acid absorbing compound.

13. The method of claim 12, wherein the drying agent is sodium sulfate.

14. The method of claim 12, wherein the acid absorbing compound is one or both of sodium carbonate and potassium carbonate.

15. The method of claim 1, wherein the sample is analyzed by a method comprising mass spectrometry.

16. The method of claim 1, wherein the sample is analyzed by a method comprising gas chromatography utilizing a mass spectra detector.

17. The method of claim 16, wherein the mass spectra detector is set to detect the radical anion of the dipicolinic diester of the electrophilic alcohol.

18. The method of claim 16, wherein the mass spectra detector uses a monitoring mode selected from low-resolution selected ion monitoring, and high-resolution selected ion monitoring.

19. The method of claim 15, wherein the analysis of the sample comprises introducing the sample by heated direct insertion probe to a mass spectrometry/mass spectrometry method of analyzing the sample.

20. The method of claim 1, wherein a high-resolution mass spectrometry method is used to analyze the sample.

21. The method of claim 1, wherein liquid chromatography/mass spectrometry methods are used to analyze the sample.

22. The method of claim 21, wherein the liquid chromatography method comprises negative-ion atmospheric pressure chemical ionization.

23. The method of claim 1, wherein two-dimensional gas chromatography with mass spectrometry is used to analyze the sample.

24. The method of claim 23, wherein the two-dimensional gas chromatography comprises using two gas chromatography columns and an effluent from the second gas chromatography column is analyzed by mass spectrometry.

25. The method of claim 1, wherein the analysis of the sample comprises ion mobility spectrometry.

* * * * *